(12) United States Patent
Bashiri et al.

(10) Patent No.: US 8,012,197 B2
(45) Date of Patent: Sep. 6, 2011

(54) HYBRID BALLON EXPANDABLE/SELF-EXPANDING STENT

(75) Inventors: Mehran Bashiri, San Carlos, CA (US); Michael L Davis, Shorewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 427 days.

(21) Appl. No.: 12/192,661

(22) Filed: Aug. 15, 2008

(65) Prior Publication Data

US 2008/0306583 A1    Dec. 11, 2008

Related U.S. Application Data

(63) Continuation of application No. 09/944,668, filed on Aug. 31, 2001, now abandoned.

(51) Int. Cl.
*A61F 2/06* (2006.01)
(52) U.S. Cl. ...................................... 623/1.18
(58) Field of Classification Search .......... 606/191, 606/194, 195; 623/1.11, 1.12, 1.15, 1.16, 623/1.18, 1.2
See application file for complete search history.

(56) References Cited

U.S. PATENT DOCUMENTS

| | | | |
|---|---|---|---|
| 5,234,456 | A | 8/1993 | Silvestrini |
| 5,441,515 | A | 8/1995 | Khosravi et al. |
| 5,591,223 | A | 1/1997 | Lock et al. |
| 5,899,935 | A | 5/1999 | Ding |
| 6,168,621 | B1 | 1/2001 | Vrba |
| 6,258,117 | B1 | 7/2001 | Camrud et al. |
| 6,350,277 | B1 | 2/2002 | Kocur |
| 6,520,984 | B1 | 2/2003 | Garrison et al. |
| 6,572,647 | B1 | 6/2003 | Supper et al. |
| 6,663,664 | B1 | 12/2003 | Pacetti |
| 2001/0000188 | A1 | 4/2001 | Lenker et al. |
| 2002/0107560 | A1 | 8/2002 | Richter |
| 2002/0177890 | A1 | 11/2002 | Lenker |

FOREIGN PATENT DOCUMENTS

| EP | 1034751 | 9/2000 |
|---|---|---|
| WO | 00/41649 | 7/2000 |

*Primary Examiner* — Eduardo C Robert
*Assistant Examiner* — David Comstock
(74) *Attorney, Agent, or Firm* — Vidas, Arrett & Steinkraus

(57) ABSTRACT

A stent comprises a tubular member having openings therein and having a plurality of interconnected members and one or more frangible restraining members. The frangible restraining members break upon partial expansion of the stent. Thereafter, the stent self-expands.

23 Claims, 6 Drawing Sheets

Fig. 8

# HYBRID BALLON EXPANDABLE/SELF-EXPANDING STENT

CROSS-REFERENCE TO RELATED APPLICATIONS

This application is a Continuation application from Ser. No. 09/944,668, filed Aug. 31, 2001, The entire contents of which is hereby expressly incorporated by reference.

BACKGROUND OF THE INVENTION

The use of endoprostheses such as stents, stent-grafts and grafts is well known in maintaining the patency of bodily vessels including blood vessels and biliary ducts. When the term 'stent' is used herein, it is to be understood in a general sense as including all such expandable prostheses, unless otherwise indicated. Typically, a stent is implanted in a vessel which has been occluded, which is subject to an aneurysm, which has a lesion present or is otherwise damaged. Often, during the implantation of the stent, the vessel will suffer from trauma. The trauma may be as a result of the dilation prior to the implantation of the stent, the presence of a foreign body (the stent) in the bodily vessel or as a result of other causes. Although it is desirable to maintain the vessel at as large a diameter as possible to minimize the possibility of restenosis, the weakening of the vessel resulting from trauma may limit the extent to which the vessel can be dilated.

The endoprostheses that are currently available include mechanically expandable stents such as balloon expandable stents, and self-expanding devices. Mechanically expandable stents are typically expanded to a desired diameter by a radially outward force to the stent with an expansion device such as a balloon. Balloon expanded stents typically are incapable of further expansion unless a balloon is reinserted in the stent and expanded. Self-expanding stents are typically made of a shape memory material or a resilient material such as spring steel. The stent is typically constrained by a sheath or other containing device which adds to the profile of the delivery catheter. Upon removal of the sheath the stent self-expands. Self-expanding stents continually exert an outward force as they try to attain their maximum possible diameter stent as well as aspects of a self-expanding stent are known. An example of a hybrid stent is described in U.S. Pat. No. 6,168,621 B1 to Vrba. Self-expanding stents which are temporarily restrained from self-expanding are also known. An example of a self-expanding stent which is restrained from, self-expanding by a coating is disclosed in U.S. Pat. No. 5,899,935. An example of a stent which is restrained from self-expanding by restraining bands which are constructed to fail is disclosed in WO 00/41649.

It would be desirable to provide an endoprosthesis which has some of the characteristics of balloon expandable stents prior to deployment thereby allowing the stent to be useable with a relatively low profile balloon catheter, but which is also capable of self-expanding following an initial balloon expansion of the stent. It is further desirable to provide an endoprosthesis which is temporarily restrained from self-expanding, which does not rely on the use of a coating for such a restraint. It is also desirable to provide an endoprosthesis requiring a force in excess of that which the endoprosthesis experiences in the body in order to break the restraining members.

The entire content of all US and foreign patents, patent applications and publications listed herein are incorporated herein by reference.

The invention in various of its embodiment is summarized below. Additional details of the invention and/or additional embodiments of the invention may be found in the Detailed Description of the Invention below.

BRIEF SUMMARY OF THE INVENTION

In one embodiment, the invention is directed to a stent comprising a non-woven tubular element having a plurality of interconnected members and at least one frangible restraining member which connects at least two interconnected members and is disposed between and not about the at least two interconnected members. Alternatively, one or more frangible restraining member may form one or more of the interconnected members or a portion thereof.

At least a portion and, optionally, the entirety of the stent is constructed and arranged to self-expand upon breaking of the frangible restraining member. The tubular element has a plurality of openings therein. Typically, the portion of the stent which is constructed and arranged to self-expand upon breaking of the frangible restraining member is made of a shape-memory material. The plurality of interconnected members and the at least one frangible restraining member may be constructed of the same material or of different materials.

The frangible restraining members may be provided in a variety of forms including in the form of frangible welds and in the form of temporary stmts. The frangible restraining members may be straight, may include one or more straight portions, may be curved or may include one or more curved portions They may be distributed helically about the stent, circumferentially about the stent, or longitudinally along the stent. Also, the frangible restraining members may be distributed uniformly throughout the stent or non-uniformly.

In another embodiment, the invention is directed to a stent comprising a generally tubular body and one or more frangible restraining members disposed about at least a portion of the tubular body. The frangible restraining member is made of the same material as the tubular body. At least a portion of the stent is capable of self-expanding upon breaking of the frangible restraining member. The generally tubular body and the frangible restraining member may be made of the same metal or polymeric material. The generally tubular body and/or the frangible members may be constructed from a material or materials having super elastic properties.

In yet another embodiment, the invention is directed to a stent comprising a generally tubular body and a metal frangible restraining member disposed about at least a portion of the tubular body. At least a portion of the stent is capable of self-expanding upon breaking of the frangible restraining member.

In those embodiments of the invention where the frangible restraining member is disposed about at least a portion of the generally tubular body, the frangible restraining member may be disposed helically about the tubular body, may be in the form of a band disposed about the circumference of the tubular member, may be in the form of longitudinal members or may be in any other suitable arrangement. The frangible restraining member may be interwoven through the tubular body or may be partially or entirely embedded therein.

In accordance with the invention, any of the inventive stents disclosed herein may be provided in embodiments in which only a portion of the stent is capable of self-expanding upon breaking of the frangible restraining member and in embodiments in which the entirety of the stent is capable of self-expanding upon breaking of the frangible restraining member.

Desirably, the inventive stents disclosed herein are capable of withstanding radially outward pressures of up to about 2 atmospheres or the equivalent force, more desirably, up to about 5 atmospheres or the equivalent force and most desirably, up to about 12 atmospheres or the equivalent force without breakage of the frangible restraining members.

The invention is also directed to a stent formed of a plurality of interconnected struts, the interconnected struts including temporary struts and permanent struts, where the temporary struts but not the permanent struts break upon the application of a predetermined radially and/or axially outward pressure to the stent.

The invention is also directed to methods of delivering a stent to a desired bodily location. In accordance with the inventive methods, a catheter with an expandable member such as a balloon is provided with any of the inventive stents disclosed herein disposed about the expandable member. The catheter is inserted in a bodily vessel and delivered to the desired bodily location. The expandable member is then expanded to break the frangible restraining member(s). Where the expandable member is in the form of a balloon, an inflation fluid is delivered to the balloon to expand it. Thereafter, the stent is allowed to self-expand. Subsequent to self-expansion of the stent a balloon or other device may be used to seat the stent into place at the desired location.

In some embodiments of the invention the stent may be constructed to achieve a memorized shape after the frangible members have been broken by applying energy, such as for example, heat, to cause the stent to expand and/or contact to the memorized shape.

Additional details and/or embodiments of the invention are discussed below.

BRIEF DESCRIPTION OF THE DRAWINGS

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The present invention, in one embodiment, is directed to a stent which includes features of a balloon expandable stent as well as features of a self-expanding stent. At least a portion of the stent is capable of self-expansion but is restrained via one or more frangible restraining members. The frangible restraining members are designed to be able to withstand the forces associated with delivery of the stent through tortuous bodily vessels and yet break when a sufficient radially and/or axially outward force is applied to the stent Desirably, the stent is delivered on a balloon based stent delivery catheter and the frangible restraining members broken upon expansion of the balloon or other application of force. Thereafter, the stent may expand to a predetermined shape.

Figure 1:
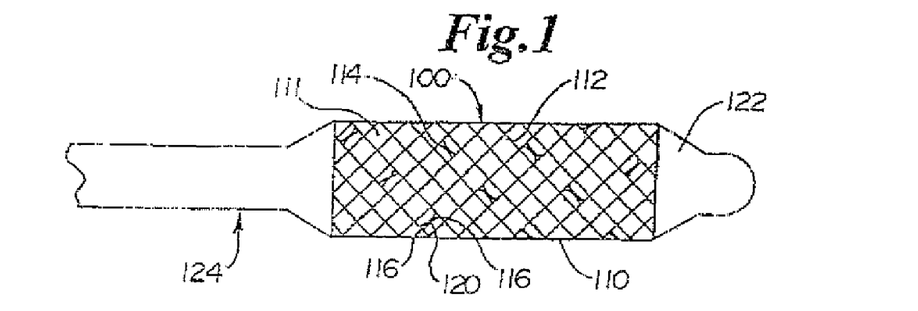
FIG. 1 is a side view of an embodiment of the invention in a reduced configuration mounted upon a balloon catheter.
Figure 2:
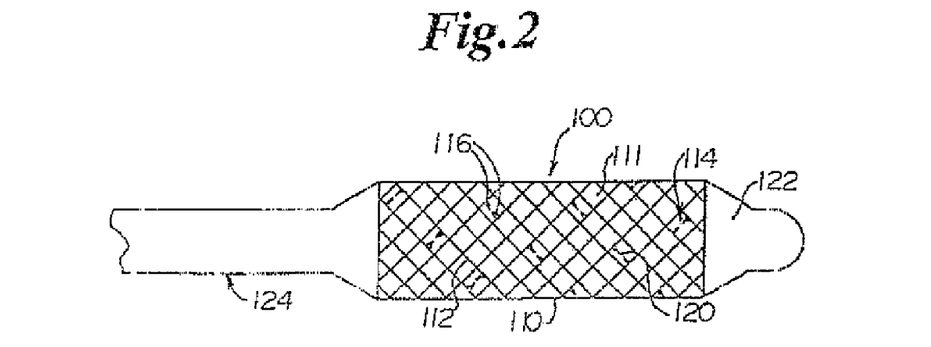
FIG. 2 is a side view of the embodiment of the invention shown in FIG. 1, following partial balloon expansion, some of the frangible restraining members having been broken.
Figure 3:
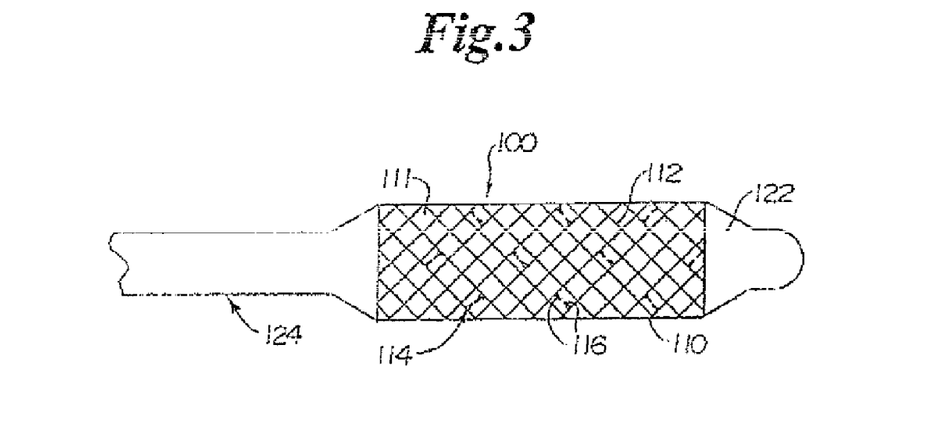
FIG. 3 is a side view of the embodiment shown in FIG. 1 immediately prior to self-expansion, all the of the frangible restraining members having been broken.

Turning to the figures in one embodiment, as shown in FIGS. 1-3, the present invention is directed to stent which includes a self-expanding tubular member 110 having a plurality of openings 111 therein and having a plurality of interconnected members 112. Interconnected members 112 intersect with one another but do not cross one another as is the case with braided stents. The stent further includes members 114 which are structurally weaker than other nearby members 112. These weaker members are hereinafter referred to as frangible restraining members 114. Frangible restraining members 114 prevent the stent from self-expanding. When frangible restraining members 114 are broken, the stent may self-expand.

The frangible restraining members 114 may be in the form of frangible welds between two or more adjacent interconnecting members 112, or may be in the form of struts which have been weakened in some manner, such as by laser etching, chemical treatment, or abrading. The interconnected members 112 and the frangible restraining members 114 may be constructed of the same or different materials.

Each frangible restraining member 114 includes two ends 116 and one or more relatively weak portions 120. Each end 116 is connected to an interconnected member 112. Frangible restraining members 114 must be strong enough to withstand any functional forces associated with delivery of the stent and any other forces experienced by the stent during delivery of the stent through the tortuous vessels of the body. The weak region 120 is designed to fail when the stent is expanded, via balloon expansion or other expansion means. Desirably, the stent is capable of withstanding radially and/or axially outward pressures of up to 2 atmospheres, or the equivalent force, more desirably, up to 5 atmospheres or the equivalent force and most desirably, up to 12 atmospheres or the equivalent force or more without breakage of the frangible restraining members. In one embodiment of the invention, an inflation pressure of at least 20 atmospheres or the equivalent force is required to break the frangible restraining members.

When stent 110 is initially subjected to an outward force, such at that supplied by balloon 122 of balloon catheter 124 as shown in FIG. 2, or by any other suitable expanding members, interconnecting members 112 reorient relative to one another to accommodate expansion of the stent. As part of the reorientation, the spacing between those interconnected members 112 which are also connected by a frangible restraining member 114 increases, thereby placing the frangible restraining member in tension, and breaking at least some of the frangible restraining members. In FIG. 2, the stent 110 is shown just prior to being fully balloon expanded and not all of the frangible members have been broken.

Figure 4:
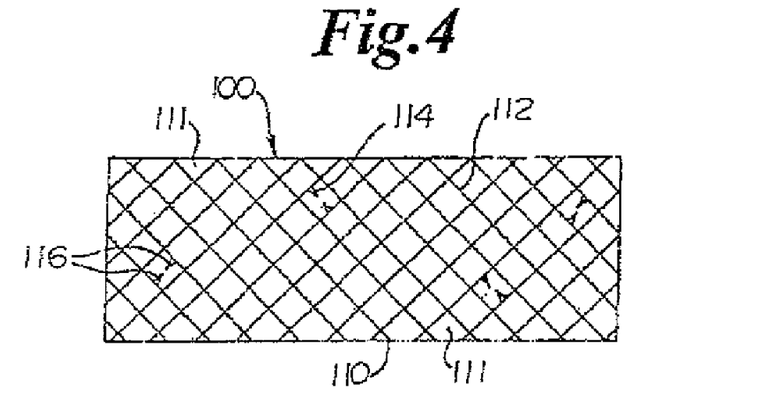
FIG. 4 is a side view of the stent shown in FIG. 1 following self-expansion of the stent.

In FIG. 3, stent 110 is shown fully balloon expanded All of the frangible restraining members 114 have broken apart and the stent is free to self-expand In FIG. 4, stent 110 is shown having self-expanded to its fully expanded state. Stent 110 is capable of self-expanding as a result of the tubular member being constructed in whole, or in part, from super elastic materials.

The term "super elastic" or "superelasticity" is used to describe the property of certain shape memory alloys to return to their original shape upon unloading after a substantially deformation while in their austenitic state, Super elastic alloys can be strained while in their austenitic state more than ordinary spring materials without being plastically deformed. This unusually large elasticity in the austenitic state is also called pseudoelasticity, because the mechanism is nonconventional in nature, or transformational superelasticity because it is caused by a stress induced phase transformation. Alloys that show superelasticity also undergo a thermoelastic martensitic transformation which is also the prerequisite for the shape memory effect. Superelasticity and shape memory effect are therefore closely related. Superelasticity can even be considered part of the shape memory effect.

The shape memory and superelasticity effect are particularly pronounced in Ni—Ti alloys and is know in other materials as well. Suitable materials include shape memory metals such as nitinol and shape memory polymers such as those disclosed in U.S. Pat. No. 5,954,744. Any super elastic material however, may be suitable for use in constructing the stent 110 and/or components thereof.

In certain embodiments of the invention, following self-expansion of the stent, portions or the entirety of the stent may be further expanded via the use of a balloon or other expansion member to seat the stent in the vessel. Alternatively, the stent may be provided with a memorized shape which may be attained through the application of energy, such as by applying heat transmitted by the delivery catheter. The ability of a stent or other implantable medical device to achieve such a memorized state is described in U.S. application Ser. No. 09/172,590, filed Oct. 14, 1998, the entire content of which is incorporated herein by reference.

Frangible restraining members 114 may be made of the same or different material as the tubular member itself. Where the tubular member is made of metal, frangible restraining members 114 may be made of the same metal as the stent or of different metals or materials. Exemplary choices of materials for the frangible restraining member include nitinol, stainless steel, platinum or tantalum. Alternatively, the frangible members 114 may be made of any metal and/or plastic material which may be characterized as soft and breakable. The frangible member 114 may be secured to the connecting members via the use of adhesives or any other suitable attachment method. Desirably, the frangible restraining member is weakened via chemical etching, laser etching or abrading in or more locations so that the restraining member is rendered frangible upon application of a desired force to the stent. The stent including the frangible members may also be integrally formed with the tubular member by cutting the stent pattern into a sheet of material and rolling the sheet to form a tube Opposing edges of the tube may then be joined together if desired or the stent may be provided in the form of a rolled sheet stent which may expand by at least partially unrolling. An example of a rolled sheet stent is disclosed in WO 01/01885. The stent including the frangible members may also be integrally formed with the tubular member by cutting the stent pattern including the frangible members into a tube.

Where the stent is made of polymeric material, the frangible restraining member(s) will be made of the same material as the tubular member and may be secured thereto via welding, the use of adhesives or any other suitable attachment method. Desirably, the restraining member is weakened via chemical etching, laser etching or abrading in or more locations so that the restraining member is rendered frangible upon application of a desired force to the stent.

The frangible restraining member may be thinned in one or more regions or the width of the frangible restraining member may be reduced in one or more regions to render the restraining member frangible. The restraining member may also be perforated in one or more regions or may have one notches therein. The extent to which the restraining member must be weakened will determine, in part, the threshold force which is required to break the frangible restraining member. The frangible restraining member is designed such that a force in excess of the forces experienced by a stent following implantation in the body must be applied to it for it to break.

Figure 5:
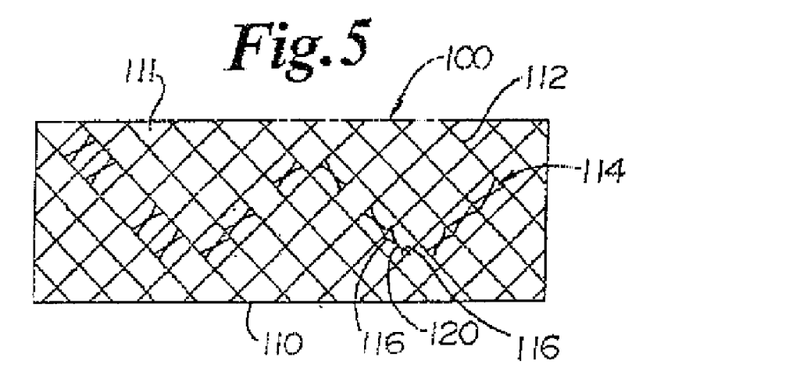
FIG. 5 is a side view of an alternative embodiment of the invention.
Figure 6:
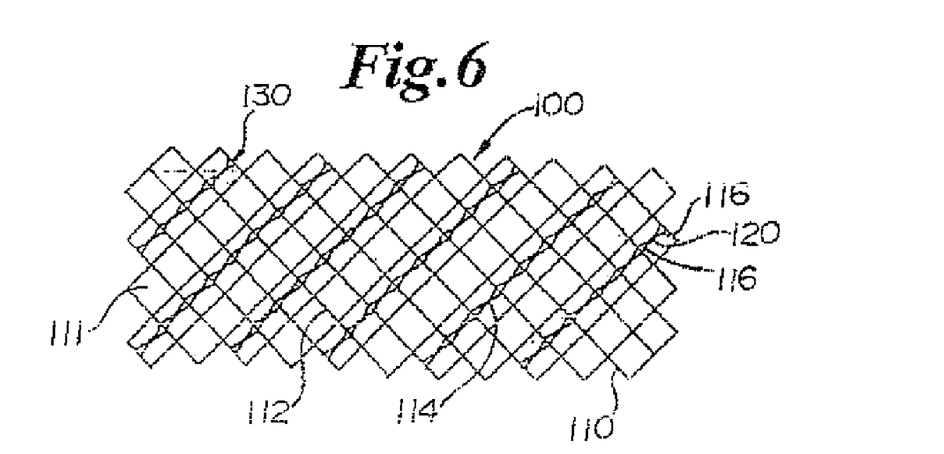
FIG. 6 is a side view of an alternative embodiment of the invention.

In accordance with the invention, frangible restraining members 114 may be distributed throughout the stent 100 in a variety of different configurations. In the embodiment shown in FIG. 5 for example, the frangible restraining members 114 are distributed intermittently about the circumference of the stent 110 in a substantially wavy pattern. In FIG. 6, the frangible restraining members 114 are distributed helically about stent 100 as shown at 130. The frangible restraining members may also be arranged circumferentially about the stent or lengthwise along the stent. Other distributions of restraining members are possible as well and are considered as being included in the scope of the present invention.

Tubular member 110 which forms a portion of the inventive stents may be of any suitable design including those designs shown in WO 96/26689, WO 01/01888, WO 99/44543, U.S. Pat. Nos. 5,733,303, 6,231,599, and 6,042,597. Any other design may also be used.

Figure 7:
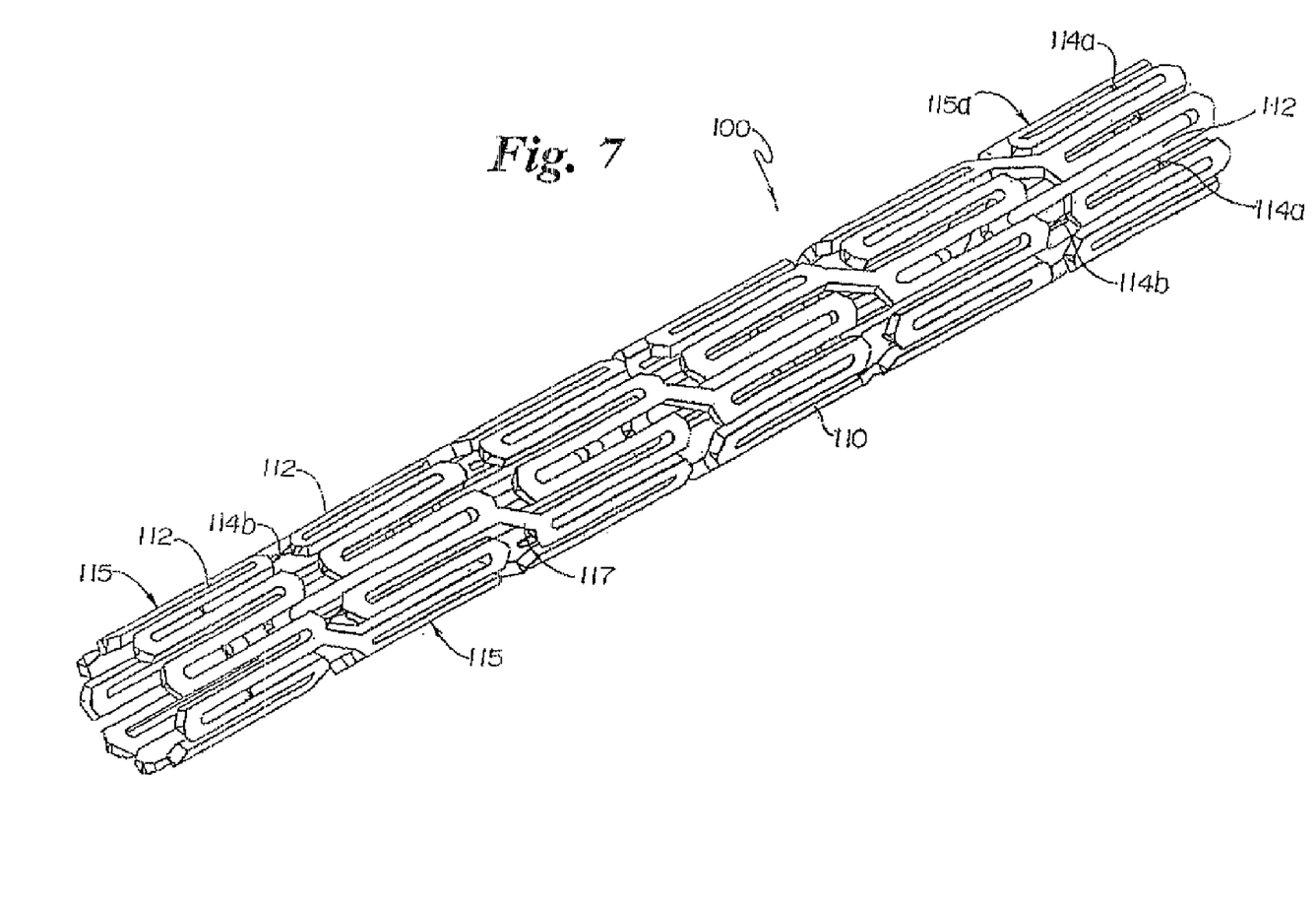
FIG. 7 is a perspective view of an alternative embodiment of the invention

In FIG. 7, a stent of the type described in WO 96/26689 is shown in an unexpanded state. Stent 100 includes a plurality of serpentine sections 115 made up of members 112. Adjacent serpentine sections are joined by connectors 117. Connectors 117 extend at an angle relative to the longitudinal axis of the stent. More generally, the stent may comprise one or more connectors between adjacent segments. The connectors may be straight or may include one or more curved portions. The ends of the each connectors may be longitudinally and/or circumferentially offset from one another.

The stent includes serpentine sections 115a with frangible restraining members 114a that extend between adjacent members 112 in the serpentine section. The stent may be comprised exclusively of sections such as serpentine section 115a or may further comprise serpentine section which lack frangible restraining members.

Further in accordance with the invention, adjacent serpentine sections may further be connected by one or more frangible restraining members 114b. The stent may also be provided in an embodiment in which the only frangible restraining members present are restraining members 114b which extend between adjacent serpentine segments.

Figure 8:
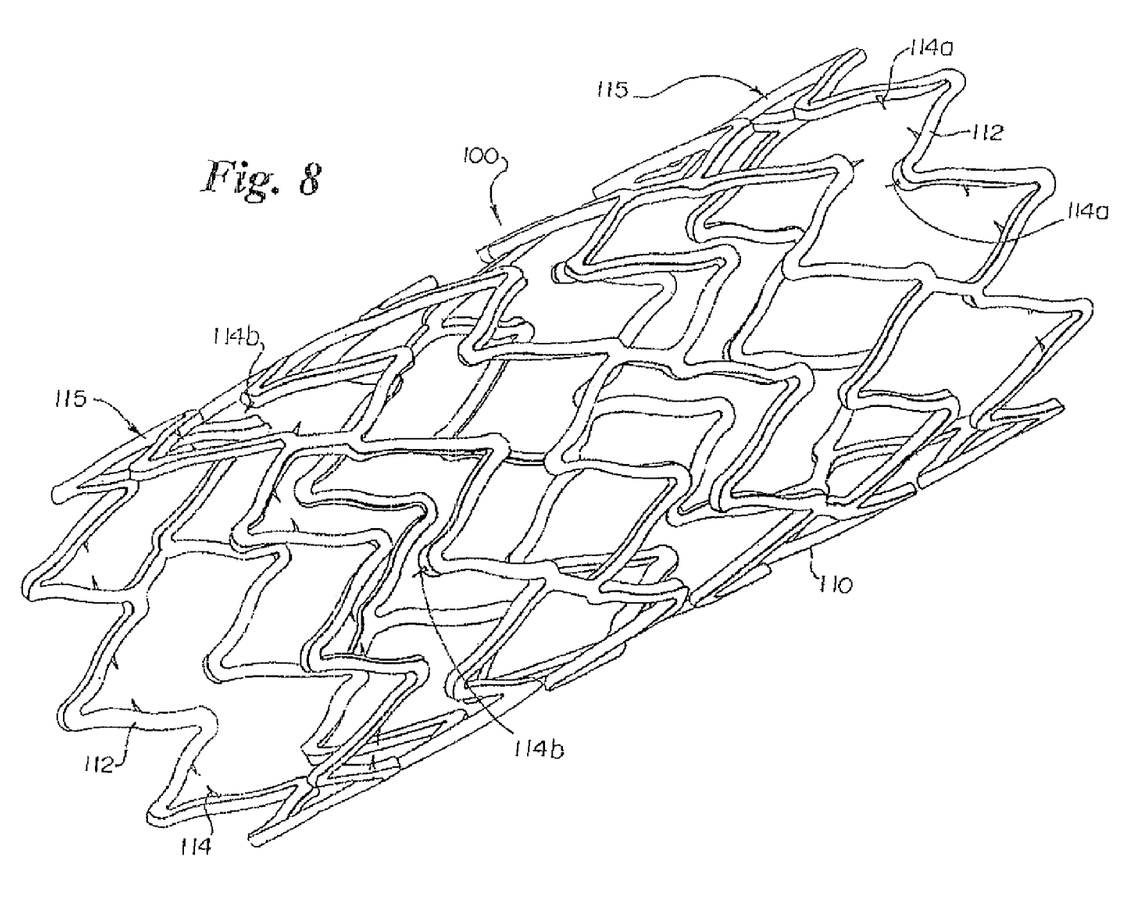
FIG. 8 is a perspective view of the embodiment shown in FIG. 7, shown subsequent to mechanical expansion of the stent.

In FIG. 8, frangible restraining members 114 have been broken as a result of mechanical expansion of the stent 110.

Figure 9:
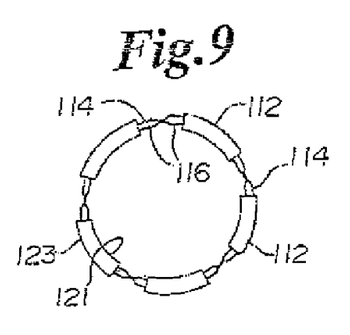
FIG. 9 is a cross-sectional view of an inventive stent prior with the frangible retaining members intact.
Figure 10:
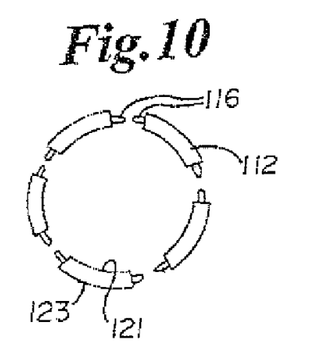
FIG. 10 is a cross-sectional view of the stent of FIG. 9 following expansion of the stent and breakage of the frangible retaining members.

Desirably, when frangible restraining members 114 break, they either extend inward toward the flow passage of the stent or they remain within the tubular envelope of the stent. In one embodiment of the invention, as shown in FIG. 9, frangible restraining members 114 are in the form of thin connectors extending between adjacent struts or members 112 of the stent. The restraining members 114 have a relatively weak portion 120 where the connector is thinned out. Following balloon expansion of the stent, as shown in FIG. 10, restraining members 114 have broken, and the ends 116 of each restraining member 114 extend from struts or members 112. Ends 116 remain within the envelope defined by inner surface 121 and outer surface 123 of the stent with ends 116 extending neither into the flow passage of the stent nor outside of the tubular wall of the stent.

In another embodiment, the invention is directed to a stent, at least a portion of which is self-expanding and which is restrained from self-expanding by one or more frangible restraining members made of the same material as the stent and which are disposed about or interspersed with the tubular surface of the stent. The frangible restraining member is designed such that a force in excess of the forces experienced by a stent following implantation. In the body must be applied to it for it to break. As shown in FIG. 10, stent 110, includes restraining member 114 helically disposed about the tubular body of the stent. When sufficient outward force is applied to the stent, frangible restraining member 114 will break and allow the self-expanding portion of the stent to self-expand.

In addition to the helical configuration of the frangible restraining member shown in FIG. 10, the frangible restraining member may be provided in other configurations as well. For example, the frangible restraining member may be in the form of one or more bands which extend about a portion or the entirety of the circumference of the stent or which weave in and out of a portion or the entirety the circumference of the stent. The frangible restraining member may also be provided. In the form of one or more longitudinal strips which prevent the stent from self-expanding. The frangible restraining members may also be provided in the form of one or more restraining members which are secured to the tubular surface of the stent and secure adjacent struts one to the other.

Figure 11:
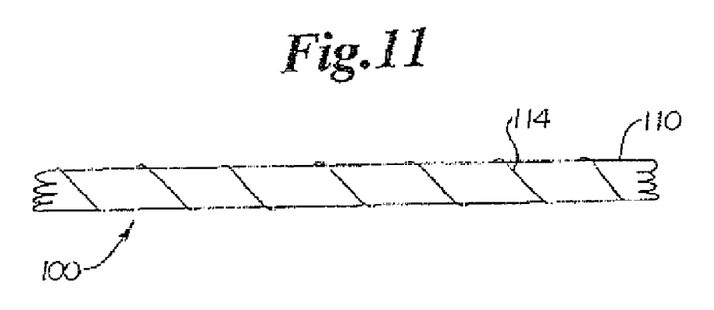
FIG. 11 is a schematic illustration of a stent comprising frangible restraining members disposed about the tubular body of the stent.

In yet another embodiment of the invention, as shown in FIG. 11, the invention is directed to a metal stent, shown generally at 100, comprising a metal tubular member 110, at least a portion of which is self-expanding and which is restrained from self-expanding by one or more metal frangible restraining members 114 which are disposed about or interspersed with the tubular member. In the embodiment of FIG. 11, frangible restraining member 114 is entirely disposed about the tubular member. The restraining member may also be provided in an arrangement in which it is disposed about portions of the tubular member and intertwined with other portions of the tubular member.

The frangible restraining member 114 may be helically disposed about the tubular as shown in FIG. 11 or may be provided in the form of one or more circumferential bands disposed about the circumference of the tubular member. The frangible restraining members may also be provided in the form of loops which tie together adjacent struts or connecting members of the tubular. Examples of such configurations may be found in WO 00/41649.

Frangible restraining members 114 may be made of the same metal as the stent or may be made of a different metal than the stent. The frangible restraining member may be secured to the stent via welding, adhesively or via any other suitable method.

Tubular member 110 may be provided with any suitable configuration including any of the designs disclosed herein or disclosed in the patents, patent applications and publications referred to herein. Furthermore, tubular member 110 may be made of any biocompatible metal including those metals disclosed herein or disclosed in the patents, patent applications and publications referred to herein.

Figure 12:
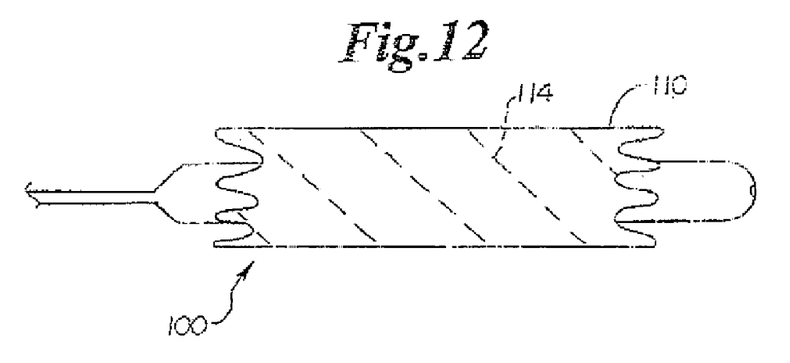
FIG. 12 is a schematic illustration of the stent of FIG. 11 following breakage of the frangible restraining members.

Stent 100 may be expanded to break the frangible members, as shown in FIG. 12. Stent 100 thereafter may self-expand.

The invention is also directed to a stent comprising a generally tubular body and one or more frangible restraining members disposed about at least a portion of the tubular body. The frangible restraining member is made of the same material as the tubular body. At least a portion of the stent is capable of self-expanding upon breaking of the frangible restraining member. The generally tubular body and the frangible restraining member may be made of the same metal or of the same polymeric material. The generally tubular body and the frangible restraining member may also be made partially of metal and partially of polymer. Any biocompatible metals and polymers suitable for use in a stent may be used including stainless steel, nitinol, tantalum and platinum. Suitable polymers include PTFE, and other polymers commonly used for grafts such as polyesters and nylons Metals and polymers other than those disclosed herein may also be used in the practice of the invention.

Figure 13:
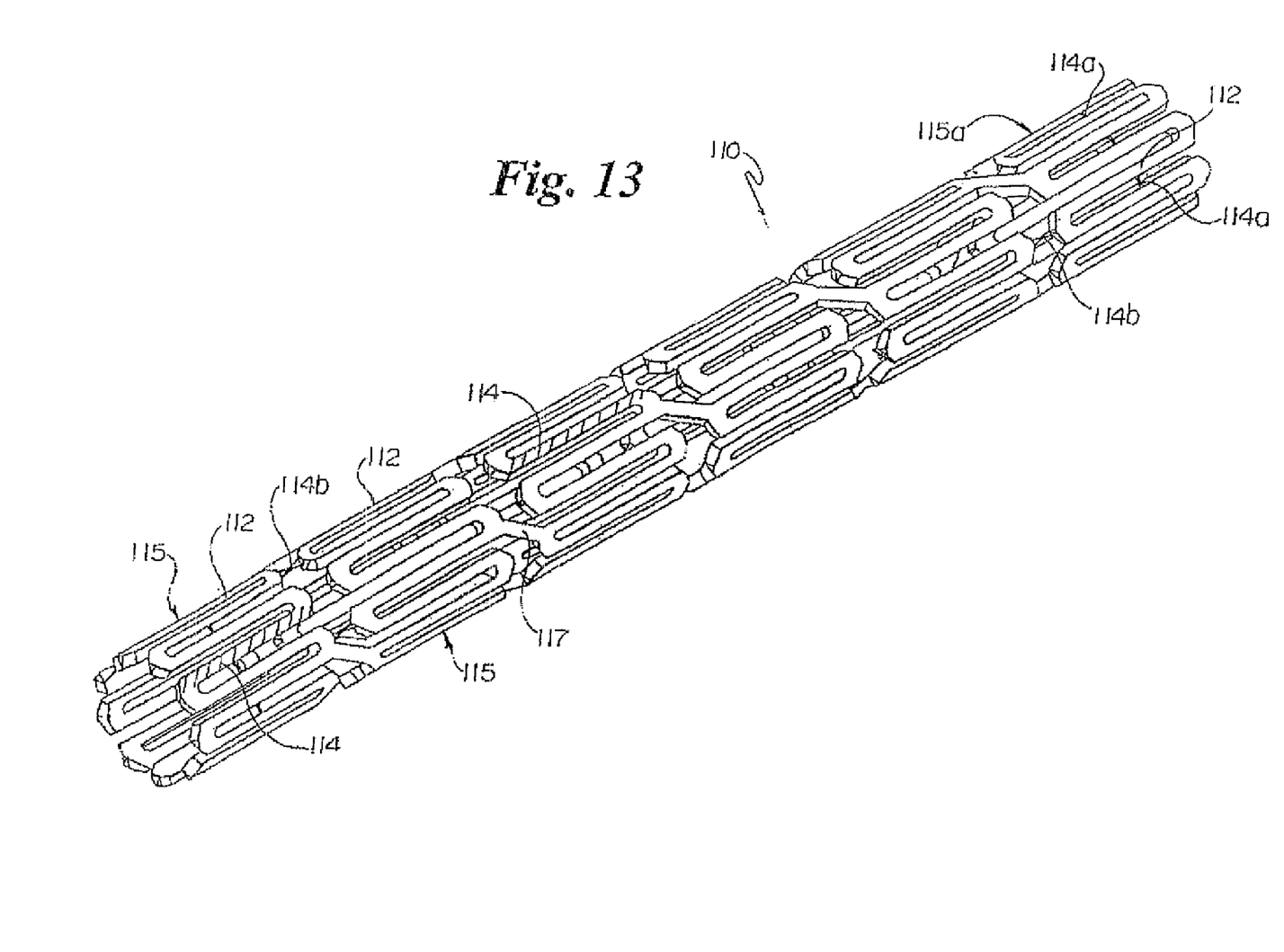
FIG. 13 is a schematic illustration of a stent comprising temporary struts in a serpentine portion of the stent.

The invention is also directed to a stent formed of a plurality of interconnected struts, the interconnected struts including temporary struts and permanent struts, where the temporary struts but not the permanent struts break upon the application of a predetermined radially and/or axially outward pressure to the stent. The stent may be made of any of the materials disclosed herein or of any other suitable stent material. The stent may be provided in any of the configurations disclosed herein or in any of the configurations disclosed in the patents, patent applications and publications disclosed herein or in any other suitable configuration. The temporary struts may be provided in the form of frangible restraining members as shown in FIGS. 1-10. The invention also contemplates replacing at least some of the permanent struts in known stent configurations with temporary struts. An example of this is shown in FIG. 13 where at least some of the serpentine segments 115 include temporary struts 114. The temporary struts may be arranged for a variety of purposes including for providing improved side branch access. Following breakage of the temporary struts, the stent may self-expand or may require additional balloon expansion.

Any of the stents disclosed herein may be provided in embodiments in which the entirety of the stent is self-expanding or in which only portions of the stent are expanding. As an example of the latter, the stent may be in the form of a bifurcated stent such that disclosed in U.S. Pat. No. 6,168,621 where the self-expanding portions have been modified in accordance with the present invention. Thus, an inventive bifurcated stent may have a self-expanding trunk portion which is restrained with frangible restraining members in accordance with the present invention and/or one or more self-expanding leg portions which are restrained by frangible restraining members as disclosed herein, where the stent has a single flow passage, a portion of the length of the stent may be self-expanding with frangible restraining members and another portion may be non-self-expanding.

The expansion properties of any of the inventive stents disclosed herein may be modified by providing a plurality of frangible retaining members which are of different strengths. Thus, one set of frangible members may be designed to break upon application of a first pressure to the stent and another set of frangible members which break upon the application of a second pressure different from the first pressure may be provided. Two, three, four or more different strength frangible members may be provided in any of the inventive stents disclosed herein. Where it is desirably to expand the first and/seconds end of the stent prior to the remainder of the stent, the first and/or second ends may be provided with weaker frangible members than the remainder of the stent. Where it is desirable to expand the central portion of the stent first, the weaker frangible members may be provided in the center of the stent. A similar effect may be achieved by varying the number of frangible members along the length of the stent. Weaker regions of the stent will have fewer frangible members than stronger portions of the stent.

The inventive stents disclosed herein may be used by themselves or as the framework for a graft. They may be for a variety of medical purposes in the body including in the coronary arteries, the peripheral arteries, arteries of the neck, cerebral arteries, veins, biliary ducts, urethras, ureters, fallopian tubes, bronchial tubes, the trachea, the esophagus and the prostate. Stents are typically placed or implanted within a bodily vessel, for example, for treating stenoses, strictures or aneurysms therein. They are implanted to reinforce collapsing, partially occluded, weakened, or dilated sections of a blood vessel. In such embodiments the frangible member(s) 114 may be imbedded into the wall of the stent/graft. The stent may act as one or more segments which provide expansion force, when the frangible member(s) are broken. In such embodiments the segments may be comprised of a super elastic material such as a Nitinol alloy.

The invention is also directed to methods of delivering a stent to a desired bodily location. In accordance with the inventive methods, a catheter with an expandable member such as a balloon is provided with any of the inventive stents disclosed herein disposed about the expandable member. The catheter is inserted in a bodily vessel and delivered to the desired bodily location. The expandable member is then expanded to break the frangible restraining members). Where the expandable member is in the form of a balloon, an inflation fluid is delivered to the balloon to expand it. Thereafter, the stent is allowed to self-expand.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to", Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims) In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 4 may be taken as alternatively dependent from claim 2 or claim 3; claim 5 may be taken as alternatively dependent on claims 2, 3, 4 or 5; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent having a longitudinal axis, the stent comprising:
a non-woven tubular element having a plurality of openings therein, the tubular element comprising a plurality of interconnected struts which form at least one continuous pathway which extends all the way around the longitudinal axis, the interconnected struts having an outside surface facing outside the stent, an inner surface facing the longitudinal axis, and a side portion therebetween, the side portion having a thickness defined by the radial distance between the outer surface and the inner surface,
wherein at least one of the interconnected struts is a frangible temporary strut, the frangible temporary strut configured to restrain at least two of the interconnected struts from self-expansion, and
wherein at least a portion of the stent is constructed and arranged to self-expand upon breaking of the at least one frangible temporary strut, the thickness of a portion of the frangible temporary strut being substantially narrower than the thickness of any other portion of the frangible temporary strut.

2. The stent of claim 1 wherein the portion of the stent which is constructed and arranged to self-expand upon breaking of the frangible temporary strut is made of a shape-memory material.

3. The stent of claim 2 wherein the shape memory material is from the group consisting of shape-memory metals and shape-memory plastics.

4. The stent of claim 1 wherein the entirety of the stent is constructed and arranged to self-expand upon breaking of the frangible temporary strut.

5. The stent of claim 1 wherein the frangible temporary strut is constructed from a different material than the interconnected struts.

6. The stent of claim 1 further comprising a plurality of frangible temporary struts, each of which extends between at least two adjacent interconnected struts.

7. The stent of claim 6 wherein the frangible temporary struts are selected from at least one member of the group consisting of: frangible welds, frangible glues, frangible solder, and any combination thereof.

8. The stent of claim 6 wherein the frangible temporary struts are distributed uniformly throughout the stent.

9. The stent of claim 6 wherein the frangible temporary struts are distributed about at least one end of the stent.

10. The stent of claim 6 wherein the stent is capable of withstanding an outward pressure of up to 2 atmospheres without breakage of the frangible temporary struts, the pressures selected from the group consisting of radial pressure, axial pressure, and any combination thereof.

11. The stent of claim 6 wherein the stent is capable of withstanding an outward pressure of up to 5 atmospheres without breakage of the frangible temporary struts, the pressures selected from the group consisting of radial pressure, axial pressure, and any combination thereof.

12. The stent of claim 6 wherein the stent is capable of withstanding an outward pressure of up to 12 atmospheres without breakage of the frangible temporary struts, the pressures selected from the group consisting of: radial pressure, axial pressure, and any combination thereof.

13. The stent of claim 1 wherein the frangible temporary strut includes a circumferential extending component.

14. The stent of claim 1 wherein the frangible temporary strut includes a curved portion.

15. A stent having a longitudinal axis, the stent comprising:
a generally non-woven tubular body having interconnected struts which form at least one continuous pathway which extends around the longitudinal axis, the interconnected struts having an outside surface facing outside the stent, an inner surface facing the longitudinal axis, and a side portion there between, the side portion having a thickness defined by the radial distance between the outer surface and the inner surface;
at least one frangible temporary strut disposed completely between at least two interconnected struts and restraining the interconnected struts from self-expansion,
wherein at least a portion of the stent is capable of self-expanding upon breaking of the at least one frangible temporary strut, the at least one frangible temporary strut being at least partially constructed from metal, the thickness of a portion of the frangible temporary strut being substantially narrower than the thickness of any other portion of the frangible temporary strut.

16. The stent of claim 15 comprising a plurality of frangible temporary struts.

17. The stent of claim 15 where the entirety of the stent is capable of self-expanding upon breaking of the frangible temporary strut.

18. The stent of claim 15 wherein the stent is capable of withstanding outward pressures of up to 2 atmospheres without breakage of the frangible temporary strut, the pressures selected from the group consisting of: radial pressure, axial pressure, and any combination thereof.

19. The stent of claim 15 wherein the stent is capable of withstanding outward pressures of up to 5 atmospheres without breakage of the frangible temporary strut, the pressures selected from the group consisting of radial pressure, axial pressure, and any combination thereof.

20. The stent of claim 15 wherein the stent is capable of withstanding outward pressures of up to 12 atmospheres without breakage of the frangible temporary strut, the pressures selected from the group consisting of radial pressure, axial pressure, and any combination thereof.

21. A non-woven stent formed of a plurality of interconnected struts and having a longitudinal axis, the interconnected struts having an outside surface facing outside the stent, an inner surface facing the longitudinal axis, and a side portion there between, the side portion having a thickness defined by the radial distance between the outer surface and the inner surface, the interconnected struts including at least one temporary strut and permanent struts, the permanent struts fully defining at least one opening in the stent, the at least one temporary strut restraining self-expansion of at least one permanent strut about the at least one opening, the at least one temporary strut but not the permanent struts breaking upon the application of a predetermined outward pressure to the stent, the thickness of a portion of the temporary strut being substantially narrower than the thickness of any other portion of the temporary strut, at least a portion of the stent constructed and arranged to self-expand upon breaking of the at least one temporary strut, no portion of the temporary strut overlapping any portion of the outer surface of the permanent struts being restrained the pressures selected from the group consisting of: radial pressure, axial pressure, and any combination thereof.

22. The stent of claim 21 wherein the predetermined outward pressure is in excess of 2 atmospheres.

23. The stent of claim 21 wherein the predetermined outward pressure is in excess of 12 atmospheres.

\* \* \* \* \*